United States Patent [19]

Barrault et al.

[11] Patent Number: 4,935,546

[45] Date of Patent: Jun. 19, 1990

[54] PROCESS FOR THE PRODUCTION OF LONG CHAIN ALKYLAMINES AND DIMETHYLALKYLAMINES AND CATALYSTS THEREFOR CATALYSTS THEREFOR

[75] Inventors: Joel Barrault, Liguge; Mongi Seffen, Tunis; Christian Forquy, Monein, all of France

[73] Assignee: Ceca, S.A., Levallois-Perret, France

[21] Appl. No.: 107,188

[22] Filed: Oct. 9, 1987

[30] Foreign Application Priority Data

Oct. 9, 1986 [FR] France ............................ 86 14044
Oct. 9, 1986 [FR] France ............................ 86 14045

[51] Int. Cl.$^5$ .................................................. C07C 85/08
[52] U.S. Cl. .................................. 564/468; 564/463; 564/480
[58] Field of Search ............................ 564/468, 480

[56] References Cited

U.S. PATENT DOCUMENTS

| | | | |
|---|---|---|---|
| 2,166,971 | 7/1939 | Schmidt et al. | 564/468 |
| 2,223,303 | 11/1940 | Lazier | 564/468 |
| 3,538,163 | 11/1970 | Rutzen et al. | 564/468 |
| 3,579,583 | 5/1971 | Rutzen | 564/468 |
| 3,579,584 | 5/1971 | Rutzen et al. | 564/468 |

FOREIGN PATENT DOCUMENTS 421718 12/1934 United Kingdom ............... 564/468

*Primary Examiner*—Glennon H. Hollrah
*Assistant Examiner*—S. Treanor
*Attorney, Agent, or Firm*—Sigalos, Levine & Montgomery

[57] ABSTRACT

A process for the production of a primary alkylamine or a dimethylalkylamine in a single stage comprising heating a reaction medium comprising a long chain carboxylic acid ester with ammonia and hydrogen in the presence of a mixed catalyst of the oxide-metal type; said oxide being titanium dioxide and the metal being a combination of copper and cobalt or of copper, chromium, and cobalt; and the mixed oxide-metal catalyst.

3 Claims, No Drawings

PROCESS FOR THE PRODUCTION OF LONG CHAIN ALKYLAMINES AND DIMETHYLALKYLAMINES AND CATALYSTS THEREFOR CATALYSTS THEREFOR

BACKGROUND OF THE INVENTION

The invention refers to a process for the direct synthesis of fatty amines from esters of fatty acids by the action of ammonia and hydrogen in the presence of mixed dehydration/hydrogenation catalysts; more particularly it is directed to the production, with a high degree of selectivity, of primary amines or dimethylated tertiary amines.

The most used industrial processes for the production of long chain amines; that is to say, those whose molecule contains from 10 to about 24 carbon atoms, are still largely based on the classic reaction of the preparation of the nitrile by reaction of ammonia on the fatty acid and dehydration, followed by hydrogenation of the nitrile thus formed. One thus obtains the long chain primary alkylamine, starting from which one goes over to the dimethylalkylamine by various procedures, of which the oldest known one is doubtlessly the one which is adapted from the Leuckart reaction, and which consists in a dimethylation of the formic acid/formaldehyde system (for instance, U.S. Pat. No. 2,366,534), with the present procedures rather using the reaction of methanol or of formaldehyde in the presence of hydrogen.

Also known are procedures for the obtaining of fatty alkylamines from fatty acids and which proceed in a single stage. They use the reaction of hydrogen and ammonia or low molecular weight amines in the presence of metallic catalysts especially with zinc-chromium or with zinc-aluminum (French Pat. No. 1,549,655), with nickel with various cocatalysts (see, for instance, East German Pat. No. 110,487), or yet based on metallic sulfides (British Pat. No. 1,135,915).

Likewise found described in the prior art are amine fabrication processes using triglycerides as raw material. (German Pat. No. 1,288,595, U.S. Pat. No. 3,579,585). The use of esters as base material for obtaining amines is cited particularly in French Pat. No. 1,598,720, U.S. Pat. No. 2,223,305, and British Pat. No. 421,718, which propose to conduct the amination reaction on mixed catalysts based on zinc or alumina.

The one stage procedures; whether they are based on the acid, the glyceride, or the esters, are evidently of a better industrial advantage than the traditional procedures which necessitate two distinct stages and two distinct catalysts: one for the dehydration into the nitrile, the other one for its hydrogenation, and a transfer of intermediate product. But they also present various drawbacks, among which for those which nevertheless underwent industrial development are the necessity of working at high temperatures and under hydrogen pressures generally above 200 bars and, above all, of not being selective; that is of delivering, in addition to the alkylamines aimed for, secondary products which it is difficult to eliminate by the usual separation methods, particularly by distillation.

SUMMARY OF THE INVENTION

The present invention alleviates these drawbacks. It permits obtaining long chain alkylamines with a very good yield and an excellent selectivity, thanks to a process functioning in a single stage and which consists of having a reaction take place at temperatures which, in any case, do not exceed 300° C., and under pressures which remain between 50 and 100 bars, between a long chain fatty acid ester and ammonia, hydrogen and, if desired, reactants whose purpose it is to improve the selectivity of the reaction, in the presence of mixed catalysts of the dehydrating/hydrogenating type.

Briefly, the present invention comprises the process for the production of a primary alkylamine or dimethylalkylamine in a single stage comprising heating a long chain carboxylic acid ester with ammonia and hydrogen in the presence of a mixed catalyst of the oxide-metal type; with the oxide being titanium dioxide and the metal being a combination of copper and cobalt or of copper, chromium, and cobalt.

The invention also comprises the novel oxide-metal type catalyst as hereinafter set forth.

DETAILED DESCRIPTION

The long chain fatty acid esters are the methyl, ethyl, propyl or butyl esters of fatty acids comprising from 10 to 24 carbon atoms and, more particularly, industrial fatty acid mixtures originating from tallow, olein, rapeseed, palm oils or coconut oils. The methyl esters are preferred and have become industrially accessible by methanolysis of fatty substances and which, being generally liquid, are more readily handled as far as the industrial manufacturing operations are concerned.

The useful catalysts for the present invention are dehydration/hydrogenation catalysts, resulting from the combination of a metal and an acid-base oxide playing in addition the role of a support. Many catalysts of this type are known, such as combinations of noble metals, of nickel, of cobalt, and of alumina, zinc oxide, chromium oxide, and the like.

It has been found that the combination of titanium oxide with copper and cobalt, and above all with copper, chromium and cobalt, results in a highly active and very selective catalyst for the conversion of the methyl esters of long chain carboxylic acids into the corresponding primary amine or dimethylamine.

The catalysts according to the invention permit conducting the reaction under the conditions of pressure noticeably lower than those of the prior art and which are between 20 and 150 bars and preferably between 50 and 100 bars, which contributes highly to reducing the formation of high molecular weight byproducts; such as the dialkylamines They contain from about 2 to 80% by weight of metals (it being understood that copper, cobalt and chromium are herein designated by the term of "metals", which definition of the term "metals" will be followed herein); one prefers, however, concentration between 10 and 50% by weight.

The cobalt amounts to about 2 to 30% of the combination of active metals; the preferred concentration being of the order of 10%. In the ternary systems which contain chromium, this metal can be present in very variable proportions which can go from about 1 to 50% of the total amount of metals present.

The reaction is oriented in decisive fashion towards the production of dimethylalkylamine by introducing methanol into the reaction medium and by using a catalyst containing from 10 to 25% of chromium; preferably a concentration in the neighborhood of 20%.

In order to orient the reaction toward the production of primary amines alone, the methanol is eliminated and a catalyst containing from 0.5 to 15% of chromium is used; preferably low concentrations of from 1 to 1.5%.

These catalysts are obtained by impregnation, precipitation, or coprecipitation on the support of the metal taken in the form of a water-soluble salt. In the mode of preparation by impregnation, the titanium oxide is put in suspension in water and the metallic salt is added to it as is or in the form of an aqueous solution. The resultant slurry or paste is evaporated entirely and the powder is dried in the drying oven in air, at about 100°–150° C., then baked, likewise in air, at about 350° C. The result constitutes the "precatalyst" ("preliminary catalyst") which is the storable form of the product and which must become the object of an activation to be carried out in the reactor. In the process by precipitation, one prepares; as previously, titanium oxide containing the salts of the catalytically-active metals, whose hydroxide is precipitated by ammonia, by operating at a temperature of about 60°–80° C. and at a maximum pH of about 7 to 8. The solid is recovered by filtration, then dried and baked as in the previously-described mode of preparation.

The invention is described hereafter in its implementation in the laboratory, transposable to the industrial scale without other preparations than those which are customary in the matter and well within the skill of those in this art without any undue experimentation.

One will find in all of the examples which are going to follow a certain number of common elements which relate to the activation of the catalyst and to the control of the reactor for the synthesis proper. They are described below.

The implementation is carried out in a reactor with fixed bed, of about 200 ml capacity, which can function under pressure and continuously. After introduction of the precatalyst (preliminary catalyst), a purge with nitrogen is carried out, at a rate of 50 1/h, at atmospheric pressure and ambient temperature.

Then the nitrogen is replaced by hydrogen, and then the temperature is raised progressively at a rate of about 4° C./min until the desired reaction temperature is reached. These temperature conditions are maintained for about 12 hours.

The temperature is then adjusted to the desired value (according to the reaction, between 250° and 350° C.) and the pressure increased to a value of the order of 50 bars.

One then introduces by means of pumps with separate membranes, the ester; the methanol (if necessary) and the liquid ammonia, by controlling the flow rates in such a way that under standard conditions for the fabrication of primary alkylamines the ratio of ester/ammonia/hydrogen is 1/10/100 or that under standard conditions for the fabrication of dimethylalkylamines the ratio of ester/methanol/ammonia/hydrogen is 1/40/10/100, and that the spatial velocity of the reaction mixture (milliliter per milliliter of catalyst and per hour) is about 1/3 h$^{-1}$.

These conditions fix only the orders of magnitude, adjustable in rather large proportions in order to take into account the special conditions of the reactions.

The gas-liquid mixture coming out of the reactor is fractionated, the liquid fraction being recovered and the gases being either discarded or recycled. The composition of the reaction products is obtained by gas chromotography analysis. Its best conditions are:

(i) column filled with CHROMOSORB WAW (Johns-Manville Corp. impregnated with CARBO-WAX 20M (Johns-Mansville Corp.), and potassium hydroxide (2%);

(ii) nitrogen as the gas carrier (30 ml/min); and (iii) temperature of the oven at equilibrium of 225° C.

The calibrations and the reaction balances are carried out with the help of aniline as an internal standard. The procedure applies both to a synthesis in closed reactor and to a continuous synthesis on a reactor with fixed bed, in which case the unconverted gases coming from the fractionation of the mixture coming out of the reactor are recycled.

The invention will be better understood from the following examples which describe syntheses of dodecylamine or of dimethyldodecylamine starting from methyl dodecanoate, without these descriptions limiting the scope of the invention to the conversion of that raw material alone.

EXAMPLE 1

(Comparative)

Operation takes place on a catalyst of composition $Cu/Al_2O_3$, 9:1/90.0%, obtained by the impregnation of alumina with cupric nitrate. The reaction is carried out at a temperature of 300° C. with a molar ratio of ester/ammonia/hydrogen of 1/10/100 and a spatial velocity of the reactant of 0.33 h$^{-1}$.

The conversion is total, but the selectivity is poor, as shown by the composition balance of the liquid effluents:

| | |
|---|---|
| dodecylamine | 72.0% |
| N-methyldodecylamine | 16.0% |
| N,N-dimethyldodecylamine | 2.5% |
| dodecylamide | 8.0% |
| dodecylnitrile | 1.0% |
| Others | 0.5% |

EXAMPLE 2

(Comparative)

If one tries to orient the reaction towards the production of dimethylamine by using a flux of reactant containing methanol, one does obtain an increase in the proportion of tertiary amine, but with just as poor a selectivity, as shown by the composition of liquid effluents obtained below on catalyst $Cu/Al_2O_3$, 17.8/82.2%, with a ratio of ester/methanol/ammonia/hydrogen of 1/40/10/100, a spatial velocity of 0.17 h$^{-1}$, and at a temperature of 250° C.:

| | |
|---|---|
| dodecylamine | 29.2% |
| N-methyldodecylamine | 34.7% |
| N,N-dimethyldodecylamine | 15.6% |
| dodecylamide | 9.1% |
| dodecylnitrile | 11.4% |

EXAMPLE 3

(Comparative)

Synthesis is conducted under the conditions of Example 1 on catalyst Cu/ZnO, 9/91%. The ester is converted at a rate of 90% but the composition of the converted fraction set forth below shows a poor yield in primary amine, above all due to the formation of amide:

| | |
|---|---|
| dodecylamine | 75.0% |
| N-methyldodecylamine | 6.7% |
| N,N-dimethyldodecylamine | 1.5% |
| dodecylamide | 14.0% |
| dodecylnitrile | 2.5% |
| Other amines | 0.3% |

EXAMPLE 4

(Comparative)

The operation, for which one hopes for a good yield in primary amine, is executed under the conditions of Example 1 on a catalyst of the copper chromite type of a composition of $Cu/Cr_2O_3$, 40/60%. Operation took place at two temperature of 300° and 350° C. The composition balance of the part of effluents corresponding to the ester effectively converted is the following:

| TEMPERATURE | 300° C. | 350° C. |
|---|---|---|
| dodecylamine | 67.0% | 74.0% |
| N-methyldodecylamine | 3.4% | 4.3% |
| N,N-dimethyldodecylamine | 15.4% | 14.5% |
| dodecylamide | 9.7% | 1.0% |
| dodecylnitrile | 3.6% | 4.7% |
| Other amines | 0.9% | 1.5% |

In both cases the selectivity is poor or very mediocre, although the degree of conversion respectively reaches 95% and 100%.

EXAMPLE 5

(Comparative)

One tries here to obtain the dimethyldodecylamine by operating likewise on a catalyst of $Cu/Cr_2O_3$, 40/60%, under conditions similar to those of Example 2, with two hydrogen/ester ratios of 100 and 400. Obtained are:

| $H_2$/ester | 100 | | 400 | |
|---|---|---|---|---|
| N-methyl-dodecylamine | 7.4% | 37.6% | 28.2% | 71.4% |
| N,N-dimethyl-dodecylamine | 30.2% | | 43.2% | |
| dodecylamine | 1.5% | | 4.9% | |
| dodecylamide | 44.2% | | 17.0% | |
| dodecylnitrile | 3.6% | | 2.5% | |
| Other amines | 13.1% | | 10.2% | |

This combination of copper-chromium oxide is advantageous in that it leads to an already non-negligible yield in methylalkylamines, but at a price of unacceptable concentrations in amide and in dialkylamines, and with a selectivity which is all the poorer as the overall yield in methylamines is better.

EXAMPLE 6

The reaction is carried out according to the invention in the presence of a catalyst prepared by coimpregnation and of a composition of $Cu/Co/TiO_2$, 20/2.5/77.5%. The reaction temperature amounts to 250° C. All of the other operating conditions are identical to those of Example 1. There are obtained:

| | |
|---|---|
| dodecylamine | 86.2% |
| N-methyldodecylamine | 2.1% |
| N,N-dimethyldodecylamine | 0.9% |
| dodecylamide | Not measurable |
| dodecylnitrile | Not measurable |
| dodecane | 1.7% |
| Other amines | 9.1% |

EXAMPLE 7

The reaction is carried out according to the invention with the help of a mixed catalyst of $Cu/Cr/Co/TiO_2$, obtained by the coimpregnation of titanium oxide and of a composition of 20/1.5/1.5/77%. The reaction temperature amounts to 250° C. All of the other conditions are those of Example 1. There are obtained:

| | |
|---|---|
| dodecylamine | 83.0% |
| N-methyldodecylamine | 4.1% |
| N,N-dimethyldodecylamine | 0.5% |
| dodecylamide | 1.0% |
| dodecylnitrile | 0.7% |
| dodecane | 8.0% |
| Other amines | 2.7% |

EXAMPLE 8

The reaction is conducted according to the invention on a catalyst of $Cu/Cr/Co/TiO_2$ of a composition by weight of 15.1/1.1/2.6/81.2, prepared by mechanical mixing of impregnation catalyst $Co/TiO_2$ and $Cu/Cr/TiO_2$. The liquid effluent has the following composition:

| | |
|---|---|
| dodecylamine | 74.5% |
| N-methyldodecylamine | 1.0% |
| N,N-dimethyldodecylamine | 1.0% |
| dodecylamide | 1.0% |
| dodecylnitrile | 1.0% |
| dodecane | 16.4% |
| Others | 5.1% |

It can be seen on this example, as on the two preceding examples that the combination of titanium oxide with metallic copper-cobalt or copper-chromium-cobalt compositions makes it possible to obtain a practically total conversion of the ester and that the long chain alkylamine formed contains minor amounts of the methylated homologs. The hydrocarbons can constitute a non-negligible part of the by-products of the reaction; they are generally not troublesome in the subsequent applications of the primary amine and in any case can easily be separated.

EXAMPLE 9

The reaction is oriented here toward the production of the dimethylalkylamine, with a catalyst according to the invention based on titanium oxide and on ternary Cu/Cr/Co highly enriched in chromium and by using a reaction medium containing methanol.

The composition by weight of the catalyst here amounts to 55.6/22.1/20.1/2.2 for $TiO_2$/Cu/Cr/Co. The conditions of the reaction are a ratio of ester/methanol/ammonia/hydrogen of 1/40/10/400, a temperature of 250° C. and a spatial velocity of 0.33 $h^{-1}$. A quasi-total conversion of the ester into dimethyldodecylamine is thus obtained. The composition of the effluents is established at:

| | |
|---|---|
| N-methyldodecylamine | 4.0% |
| N,N-dimethyldodecylamine | 93.0% |
| dodecylamine | 1.5% |
| dodecylamide | 0.5% |
| dodecylnitrile | Not measurable |
| Other amines | Not measurable |
| dodecane | 1.0% |

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for the production of a primary alkylamine or a dimethylalkylamine in a single stage with a high selectivity comprising heating a reaction medium comprising a long chain carboxylic acid methyl ester with ammonia and hydrogen in the presence of a mixed titanium oxide-metal catalyst containing from about 10 to 50% by weight metals and the balance titanium dioxide and the metal is a combination of copper and cobalt or of copper, chromium, and cobalt, the temperature of said reaction medium not exceeding 300° C., and the total pressure being between about 50 to 100 bars.

2. The process of claim 1, for the preferred production of dimethylalkylamines, wherein the reaction medium also contains methanol and the proportion by weight of the chromium in the catalyst is between about 10 and 25%.

3. The process of claim 1, for the preferred production of monoalkylamines, wherein the reaction medium contains ammonia and hydrogen to the exclusion of methanol, and the proportion by weight of the chromium in the catalyst is between about 0.5 and 15%.

* * * * *

UNITED STATES PATENT AND TRADEMARK OFFICE
CERTIFICATE OF CORRECTION

PATENT NO. : 4,935,546

DATED : June 19, 1990

INVENTOR(S) : Barrault, et al

It is certified that error appears in the above-identified patent and that said Letters Patent is hereby corrected as shown below:

Cover page, [75] nationality of inventors change Mongi Seffen nationality and residence to read -- Tunisia.

Signed and Sealed this

Twenty-fourth Day of September, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,935,546

DATED : June 19, 1990

INVENTOR(S) : Barrault, et al

It is certified that error appears in the above-identified patent and that said Letters Patent is hereby corrected as shown below:

Cover page, [75] nationality of inventors change Mongi Seffen nationality and residence to read -- Tunisia.

Signed and Sealed this

Twenty-fourth Day of September, 1991

*Attest:*

HARRY F. MANBECK, JR.

*Attesting Officer*   Commissioner of Patents and Trademarks